United States Patent
Ruchti et al.

(10) Patent No.: US 7,698,105 B2
(45) Date of Patent: Apr. 13, 2010

(54) METHOD AND APPARATUS FOR IMPROVING PERFORMANCE OF NONINVASIVE ANALYTE PROPERTY ESTIMATION

(75) Inventors: Timothy L. Ruchti, Gilbert, AZ (US);
Linda Hockersmith, Tempe, AZ (US);
Stephen L. Monfre, Gilbert, AZ (US);
Kevin H. Hazen, Gilbert, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 1325 days.

(21) Appl. No.: 11/168,941

(22) Filed: Jun. 27, 2005

(65) Prior Publication Data

US 2006/0264718 A1 Nov. 23, 2006

Related U.S. Application Data

(60) Provisional application No. 60/683,848, filed on May 23, 2005.

(51) Int. Cl.
*G06F 11/00* (2006.01)
*A61B 5/00* (2006.01)

(52) U.S. Cl. .................. 702/185; 600/310
(58) Field of Classification Search .............. 702/77, 702/185, 189; 600/310, 316, 322, 473; 250/339.11, 250/339.12
See application file for complete search history.

(56) References Cited

U.S. PATENT DOCUMENTS

| | | | | |
|---|---|---|---|---|
| 6,040,578 | A * | 3/2000 | Malin et al. | 250/339.12 |
| 7,519,406 | B2 * | 4/2009 | Blank et al. | 600/310 |
| 2005/0119541 | A1 * | 6/2005 | Lorenz et al. | 600/316 |

* cited by examiner

*Primary Examiner*—Bryan Bui
(74) *Attorney, Agent, or Firm*—Michael A. Glenn; Glenn Patent Group

(57) ABSTRACT

The invention relates to noninvasive analyte property determination. More particularly, the invention relates to a method and apparatus for performing conditional additional acquisition of noninvasive spectra to improve analyzer performance. Conditional additional data acquisition is used to confirm, update, and/or supplement spectral data.

24 Claims, 2 Drawing Sheets

METHOD AND APPARATUS FOR IMPROVING PERFORMANCE OF NONINVASIVE ANALYTE PROPERTY ESTIMATION

CROSS REFERENCE TO RELATED APPLICATIONS

This application claims priority to U.S. provisional patent application No. 60/683,848 filed May 23, 2005.

BACKGROUND OF THE INVENTION

Field of the Invention

Sampling Methodology

A wide range of technologies serve to analyze the chemical make-up of the body. These techniques are broadly categorized into two groups, invasive and noninvasive. Herein, a technology that acquires any biosample from the body for analysis, beyond calibration, or if any part of the measuring apparatus penetrates through the outer layers of skin into the body, the technology is referred to as invasive. Thus, the classes of minimally invasive techniques and partially implantable devices are invasive techniques. A particular analyte property determined invasively and/or noninvasively is glucose concentration in blood/tissue.

Invasive Type Analyte Property Estimation

Invasive and minimally invasive technologies require a sample, which takes time and effort to acquire and/or to prepare. Often the time required is on the scale of a minute or longer and effort typically requires drawing or sampling in an invasive manner a biological fluid. In addition, the acquired sample is analyzed using techniques, such as chemical analyses, that require time. Exemplary techniques include colorimetric and enzymatic analyses. Still further, these sampling techniques are costly in quantity. The aforementioned time and resource requirements combine to limit the number of replicate samples that are sampled using invasive techniques. In a first example, invasive and minimally invasive blood glucose concentration analyzers sample blood or interstitial fluid that is removed from the body by means, such as suction, a lancet, laser poration, or application of current by iontophoresis. In many cases, the sample collection technique requires considerable time for acquisition. In a first case, the iontophoresis based analyzer of Cygnus (Redwood City, Calif.) provides only one reading every twenty minutes, each delayed by at least ten minutes due to the measurement process. This measurement is made through an alternative invasive electrochemical-enzymatic sensor on a sample of interstitial fluid, which is drawn through the skin using iontophoresis. Consequently, the limitations of the device include the potential for significant skin irritation, collection of a biohazard, and a limit of three readings per hour. A second case is the class of semi-implantable glucose analyzers based upon open-flow microperfusion. Again, these analyzers require tens of minutes for sample acquisition. A third case is the MiniMed (Northridge, Calif.) continuous glucose monitoring system, a short-term implantable that acquires a glucose concentration every five minutes. Again, all of these invasive analyte property estimations require time and money for replicate analysis. None of these technologies are spectrophotometric based or offer rapid or continuous glucose concentration determination.

Noninvasive Type Analyte Property Estimation

There exist a number of noninvasive approaches for analyte property estimation in tissue or blood. These approaches vary widely but have at least two common steps. First, an apparatus is used to acquire a photometric signal from the body. Second, an algorithm is used to convert this signal into a analyte property determination.

One type of noninvasive analyte property analyzer is a noninvasive glucose concentration analyzer, which estimates a glucose concentration from spectra of a body part. Typically, a noninvasive apparatus uses some form of spectroscopy to acquire a signal, such as a spectrum, from the body. A particular range for noninvasive glucose concentration determination in diffuse reflectance mode is in the near-infrared from approximately 1100 to 2500 nm or one or more ranges therein, see K. Hazen, *Glucose Determination in Biological Matrices Using Near-Infrared Spectroscopy*, doctoral dissertation, University of Iowa (1995). These techniques are distinct from the traditional invasive and alternative invasive techniques in that the interrogated sample is a portion of the human body in-situ, not a biological sample acquired from the human body.

Data Processing

Several approaches exist that employ diverse preprocessing methods to remove spectral variation related to the sample and instrument variation including normalization, smoothing, derivatives, multiplicative signal correction, [P. Geladi, D. McDougall, H. Martens, *Linearization and scatter-correction for near-infrared reflectance spectra of meat*, Applied Spectroscopy, vol. 39, 491-500, (1985)], standard normal variate transformation, [R. Barnes, M. Dhanoa, S. Lister, *Applied Spectroscopy*, 43, 772-777, (1989)], piecewise multiplicative scatter correction, [T. Isaksson and B. Kowalski, *Applied Spectroscopy*, 47, 702-709, (1993)], extended multiplicative signal correction, [H. Martens, E. Stark, *J. Pharm Biomed Anal*, 9, 625-635, (1991)], pathlength correction with chemical modeling and optimized scaling, [*GlucoWatch automatic glucose biographer and autosensors*, Cygnus Inc., Document #1992-00, Rev. March (2001)], and finite impulse response filtering, [S. Sum, *Spectral signal correction for multivariate calibration*, Doctoral Dissertation, University of Delaware, (1998); S. Sum, and S. Brown, *Standardization of fiber-optic probes for near-infrared multivariate Calibrations, Applied Spectroscopy*, Vol. 52, No. 6, 869-877, (1998); and T. Blank, S. Sum, S. Brown, S. Monfre, *Transfer of near-infrared multivariate calibrations without standards, Analytical Chemistry*, 68, 2987-2995, (1996)].

In addition, a diversity of signal, data, or pre-processing techniques are commonly reported with the fundamental goal of enhancing accessibility of the net analyte signal [D. Massart, B. Vandeginste, S. Deming, Y. Michotte, L. Kaufman, *Chemometrics: a textbook*, New York, Elsevier Science Publishing Company, Inc., 215-252, (1990); A. Oppenheim, R. Schafer, *Digital Signal Processing*, Englewood Cliffs, N.J.: Prentice Hall, 1975, 195-271; M. Otto, *Chemometrics*, Weinheim: Wiley-VCH, 51-78, (1999); K. Beebe, R. Pell, M. Seasholtz, *Chemometrics A Practical Guide*, New York: John Wiley & Sons, Inc., 26-55, (1998); M. Sharaf, D. Illman and B. Kowalski, *Chemometrics*, New York: John Wiley & Sons, Inc., 86-112, (1996); and A. Savitzky, M. Golay, *Smoothing and differentiation of data by simplified least squares procedures*, Anal. Chem., vol. 36, no. 8, 1627-1639, (1964)]. A goal of these techniques is to attenuate the noise and instrument variation while maximizing the signal of interest.

The aforementioned methods for preprocessing partially compensate for variation related to instrument and physical changes in the sample and enhance the net analyte signal in the presence of noise and interference.

Calibration/Analysis

One noninvasive technology, near-infrared spectroscopy, has been heavily researched for its application for both frequent and painless noninvasive measurement of glucose. This approach involves the illumination of a spot on the body with near-infrared (NIR) electromagnetic radiation, light in the wavelength range of 700 to 2500 nm. The light is partially absorbed and scattered, according to its interaction with the constituents of the tissue. With near-infrared spectroscopy, a mathematical relationship between an in-vivo near-infrared measurement and the actual blood glucose concentration needs to be developed. This is achieved through the collection of in-vivo NIR measurements with corresponding blood glucose concentrations that are obtained directly through the use of measurement tools, such as any appropriate and accurate traditional invasive or alternative invasive reference device.

For spectrophotometric based analyzers, there are several univariate and multivariate methods that can be used to develop this mathematical relationship. However, the basic equation which is being solved is known as the Beer-Lambert Law. This law states that the strength of an absorbance/reflectance measurement is proportional to the concentration of the analyte which is being measured as in equation 1, $$A = \epsilon b C \quad (1)$$

where A is the absorbance/reflectance measurement at a given wavelength of light, $\epsilon$ is the molar absorptivity associated with the molecule of interest at the same given wavelength, b is the distance or pathlength that the light travels, and C is the concentration of the molecule of interest, such as glucose.

Chemometric calibration techniques extract the glucose related signal from the measured spectrum through various methods of signal processing and calibration including one or more mathematical models. Common multivariate approaches requiring a set of exemplary reference glucose concentrations and an associated sample spectrum include partial least squares (PLS) and principal component regression (PCR). Many additional forms of calibration are well known in the art such as neural networks.

Diabetes

A particular disease of interest for monitoring and control with noninvasive analyzers is diabetes mellitus. Diabetes is a chronic disease that results in abnormal production and use of insulin, a hormone that facilitates glucose uptake into cells. While a precise cause of diabetes is unknown, genetic factors, environmental factors, and obesity play roles. Diabetics have increased risk in three broad categories: cardiovascular heart disease, retinopathy, and neuropathy. Diabetics often have one or more of the following complications: heart disease and stroke, high blood pressure, kidney disease, neuropathy, retinopathy, diabetic ketoacidosis, skin conditions, gum disease, impotence, and fetal complications. Diabetes is a leading cause of death and disability worldwide. Moreover, diabetes is merely one among a group of disorders of glucose metabolism that also includes impaired glucose tolerance and hyperinsulinemia, which is also known as hypoglycemia.

Diabetes Prevalence and Trends

The prevalence of individuals with diabetes is increasing with time. The World Health Organization (WHO) estimates that diabetes currently afflicts 154 million people worldwide. There are 54 million people with diabetes living in developed countries. The WHO estimates that the number of people with diabetes will grow to 300 million by the year 2025. In the United States, 15.7 million people or 5.9 percent of the population are estimated to have diabetes. Within the United States, the prevalence of adults diagnosed with diabetes increased by 6% in 1999 and rose by 33% between 1990 and 1998. This corresponds to approximately eight hundred thousand new cases every year in America. The estimated total cost to the United States economy alone exceeds $90 billion per year. *Diabetes Statistics*, National Institutes of Health, Publication No. 98-3926, Bethesda, Md. (November 1997).

Long-term clinical studies demonstrate that the onset of diabetes related complications is significantly reduced through proper control of blood glucose concentrations. The Diabetes Control and Complications Trial Research Group, *The effect of intensive treatment of diabetes on the development and progression of long-term complications in insulin-dependent diabetes mellitus*, N. Eng. J. of Med., 329:977-86 (1993); U.K. Prospective Diabetes Study (UKPDS) Group, *Intensive blood-glucose control with sulphonylureas or insulin compared with conventional treatment and risk of complications in patients with type 2 diabetes*, Lancet, 352:837-853 (1998); and Y. Ohkubo, H. Kishikawa, E. Araki, T. Miyata, S. Isami, S. Motoyoshi, Y. Kojima, N. Furuyoshi, M. Shichizi, *Intensive insulin therapy prevents the progression of diabetic microvascular complications in Japanese patients with non-insulin-dependent diabetes mellitus: a randomized prospective 6-year study*, Diabetes Res. Clin. Pract., 28:13-117 (1995).

Many glucose meters have reduced accuracy when glucose concentrations are low. To offset significant errors at low glucose concentration, device labeling often encourage the user or operator to use symptoms in addition to the device reading to verify hypoglycemic glucose concentration results. However, a true verification requires users to perform a second test. In traditional invasive techniques, a second test requires a second lancing procedure and the use of a second test strip, which results in additional pain and an added financial cost, respectively. As discussed infra, minimally invasive techniques often require a biosample that is accumulated or measured over a period of several minutes to upwards of twenty minutes. Therefore, one or more replicate measurements using these minimally invasive techniques is not practical. As a result, many people do not perform a second test to verify reported glucose concentrations.

Currently there exists a need for analyzers to easily confirm, update, and/or enhance output of estimated analyte property values under one or more conditions.

SUMMARY OF THE INVENTION

The invention relates to both noninvasive analyte property determination and estimation. More particularly, the invention relates to a method and apparatus for performing conditional additional acquisition of noninvasive spectra to improve analyzer performance. Conditional additional data acquisition is used to enhance analyzer performance by confirming, updating, and/or supplementing spectral data.

DETAILED DESCRIPTION OF THE INVENTION

Figure 1:
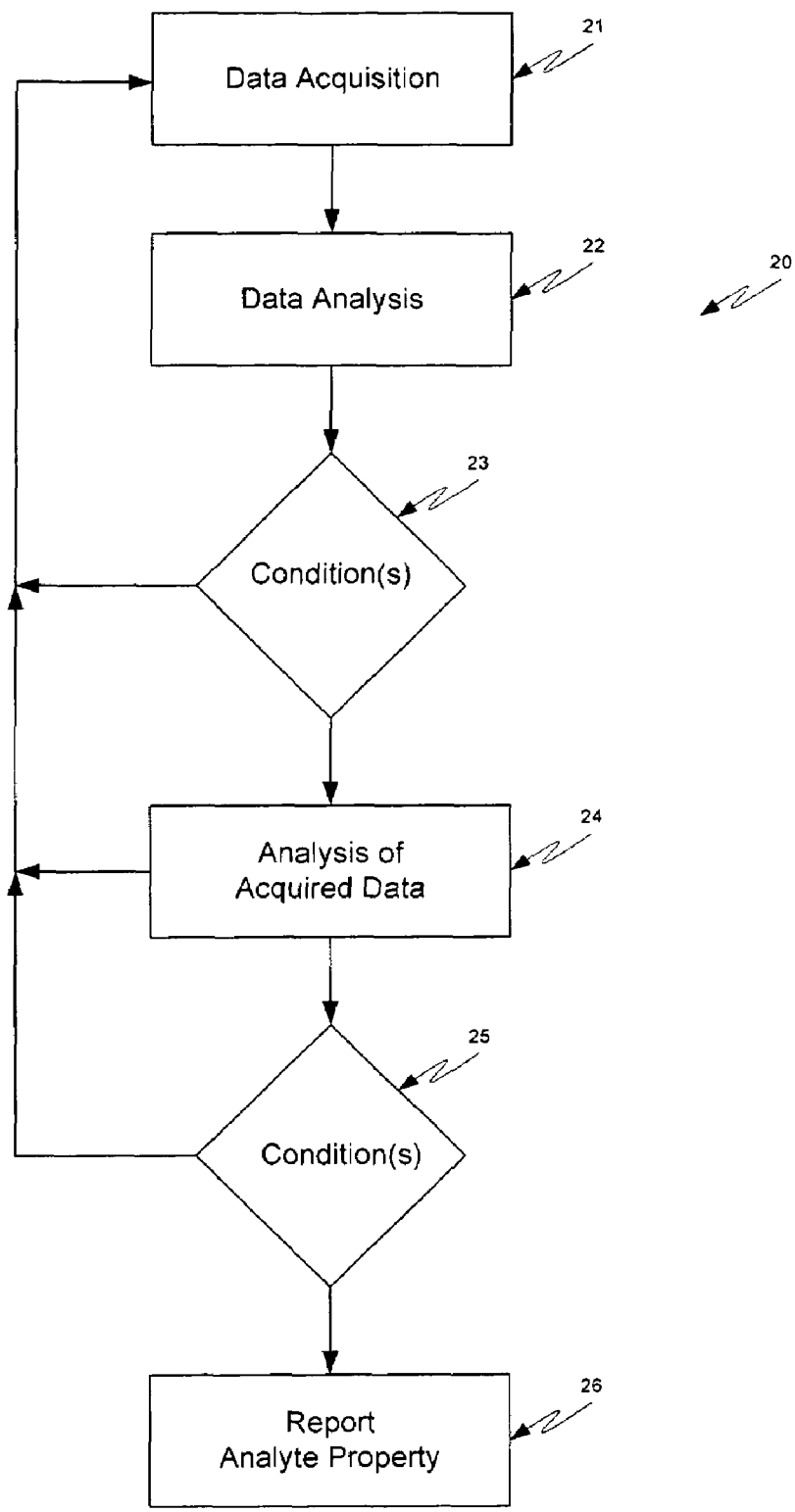
FIG. 1 provides an exemplar block diagram of conditional data acquisition according to the invention.

Currently there exists a need for analyzers to confirm, update, or enhance output of an analyte property under one or more conditions. For example, under certain conditions it is extremely advantageous to clinical management of certain diseases if test results are more accurate and/or precise, if the test results are easily and/or automatically verified, and/or if the test results are updated in a timely fashion.

Estimation of an analyte property from noninvasive spectra using an algorithm is a complex task. In some instances, the estimated property is erroneous. In other instances, unacceptable errors exist in the estimated analyte property value. In still yet another instance, verification of the reported result is beneficial. In yet another instance, enhanced precision of analyte property estimation, such as glucose concentration near hypoglycemic levels, is used to enhance disease management. A set of rules or conditions is used to minimize erroneous results, to collect replacement or supplemental spectra to replace estimations in real time, to enhance the precision and/or accuracy of the analyte property estimation, and/or to provide verification of results. In one case, the conditions direct the analyzer to collect at least one replacement spectrum. In a second case, the conditions direct the analyzer to collect at least one supplemental spectrum. In a third case, the conditions direct collection of at least one verification spectrum. The algorithm uses the earlier acquired spectra, replacement spectra, supplemental spectra, and/or verification spectra to report an updated analyte property estimation.

In its broadest sense, the invention uses an analyzer to collect at least one noninvasive spectrum. An algorithm is used to generate an estimate of an analyte property using the noninvasive spectrum. Conditions are employed to determine if supplemental noninvasive spectra and corresponding analyte property estimation is beneficial. The conditions are based upon the current analyte property estimation with or without the use of previous analyte property estimations. The analyte property, analyzer, and algorithm are further described, infra.

EXAMPLE I

An initial example is used to illustrate one aspect the invention. For some analyte property estimations, such as noninvasive glucose concentration estimation, disease treatment is sensitive to the precision and/or accuracy of the measurement. For instance, at hypoglycemic glucose concentrations, such as glucose concentrations of less than 70 mg/dL, treatment is ingestion of carbohydrates. As optimal glucose concentrations are only slightly higher in the 70 to 120 mg/dL range, ingestion by diabetics of even a minimal amount of carbohydrates often results in glucose concentrations that are higher than 120 mg/dL. Achieving glucose concentrations in the range of 70 to 120 mg/dL, is of prime importance in maintaining tight control of diabetes mellitus. Therefore, false negative reporting of hypoglycemic glucose concentrations below 70 mg/dL when the actual glucose concentration is in the normal range of 70 to 120 mg/dL, is detrimental. A decrease in false negative reporting results from enhanced precision of glucose concentration estimation below a threshold, such as a threshold set in the normal glucose concentration range. As described herein, enhanced precision is achieved by conditionally collecting additional spectra.

In one particular case, a condition is preset that if the estimated glucose concentration is less than a threshold, such as about 70, 90, 110, or 130 mg/dL, then a supplemental estimation is generated from a second spectrum or set of spectra, and an average glucose concentration of the original and supplemental glucose concentrations is reported to the user. The average concentration is statistically more precise and accurate. In this example, a simple average concentration is calculated for the particular analyte glucose. The threshold condition for calling for a supplemental reading is optionally based upon precision or performance of the analyzer. The average concentration yields a more precise glucose concentration resulting in fewer false negative, reports of hypoglycemic glucose concentration, allowing for enhanced management of diabetes mellitus by optimizing the period of time that an individual remains in a normal glucose concentration range. This example is illustrative in nature and is not intended to limit the scope of the invention.

Some spectroscopic analyzers are capable of rapid collection of spectra and rapid estimation of a glucose concentration from the acquired spectra. For instance, with an array detector noninvasive spectra with high signal-to-noise ratios are collected in a very short time period, such as about seconds to fractions of a second. Multiplexed analyzers, such as those described in U.S. patent application Ser. No. 10/472, 856 filed Mar. 7, 2003, which is incorporated herein it its entirety by this reference thereto, are capable of data collection in short time periods, such as about 0.001, 0.01, or 0.1 seconds. This allows real-time or almost real-time assessment of the estimated glucose concentration and the ability to rapidly collect and analyze one or more subsequent or confirmation readings.

Analyte Property

In its broadest sense, any chemical constituent or physical property of the body is a potential analyte. Common examples include: temperature, pH, a tissue constituent, a blood constituent, a protein, a fat, a glucose related metabolite, glucose, urea, an anion, a cation, and a salt. Herein, the analyte property glucose concentration is used in an exemplary fashion. Use of glucose in the examples herein is not intended to limit the scope of the invention.

Analyte Estimation

FIG. 1 illustrates an exemplary flow of data collection and analysis 20 An analyzer is configured to acquire data 21, and optionally to analyze the collected data 22. The optional data analysis 22 is performed during and/or after data acquisition 21. At least one of the spectral data 20, the analyzed data 21, sample replicate number, and/or analyte property estimation is compared against one or more conditions. The conditions 23 determine if any replacement, verification, and/or supplemental spectra are to be collected in a second data acquisition step 21. The optional second spectrum or set of spectra is used to replace, verify, or supplement the original spectrum or spectra. The optional second data analysis step 22 is performed during or after the second data acquisition step 21. The conditional collection of data is repeated n times, where n is an integer greater than or equal to zero. For each iteration, the first condition or set of conditions 23 is used or a $n^{th}$ condition or set of conditions 23 is used. Optionally, a resulting spectrum or a resulting analyte property is acquired and analyzed 24 against a second layer of conditions 25 having the ability to direct additional data acquisition 21. Ultimately, an analyte property is generated and reported 26. The replacement or supplemental data are used with or without the original data to enhance precision of the estimated analyte property.

Analyzer

A noninvasive analyzer is used to acquire noninvasive spectra of the body, tissue, and/or skin representative of the analyte property. The analyzer analyzes a sample site, which is a portion of tissue of the subject that is irradiated by a source, and wherein a portion of the irradiated light entering the tissue is collected and detected. Tissue sites include any of: a hand, finger, palmar region, base of thumb, forearm, volar aspect of the forearm, dorsal aspect of the forearm, upper arm, head, earlobe, eye, tongue, chest, torso, abdominal region, thigh, calf, foot, plantar region, and toe. Types of noninvasive analyzers are described, infra.

Figure 2:
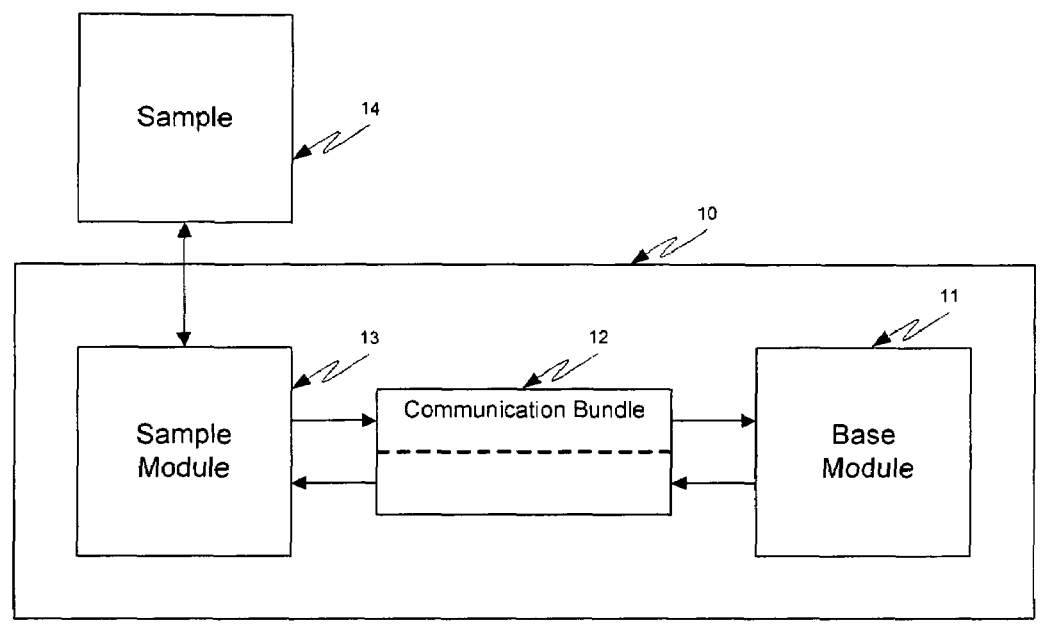
FIG. 2 provides an illustrative block diagram of an analyzer according to the invention.

Referring now to FIG. 2, an analyzer is presented. An analyzer includes at least a source, a sample interface, at least one detector, and an associated algorithm. Typically, all of the components of the analyzer are included in a single unit. In FIG. 1, an analyzer 10 is presented in terms of a base module 11, a communication bundle 12, and a sample module 13. The sample module, also referred to as a sampling module, interfaces to a sample 14 and, optionally at the same or different times to one or more reference materials. Herein, the combined base module 11, communication bundle 12, sample module 13, and algorithm is referred to as a spectrometer and/or analyzer 10.

In the case of an analyzer 10 contained in a single unit, the base module 11, communication bundle 12, and sample module 13 are all integrated together and are contained within or integrated onto a single containing unit. Alternatively, the base module 11 is separated from the sample module 13. Communication exists between the sample module 13 and base module 11 and is presented here schematically as a communication bundle 12. In varying embodiments, the communication bundle is wireless, carries electrical power, carries data, transmits energy or movement, and/or carries fluid. For example, the communication bundle 12 carries feedback control signals, temperature sensing data, coupling fluid, light, data, and/or contains hydraulic fluid.

The invention includes a number of analyzer or spectrometer configurations for collecting noninvasive spectra of regions or volumes of the body. Typically, a spectrometer has one or more beam paths from a source to a detector. Examples of a light source include: a blackbody source, a tungsten-halogen source, one or more LED's, and one or more laser diodes.

Examples of sample interfaces include: a contacting optic, a free-space optical system, use of a coupling fluid, a dynamic sample probe, and use of one or more fiber optics. For multi-wavelength spectrometers, a wavelength selection device or a series of optical filters are optionally used for wavelength selection.

Wavelength selection devices include dispersive elements, such as one or more plane, concave, ruled, or holographic grating. Additional wavelength selective devices include an interferometer, successive illumination of the elements of a light emitting diode (LED) array, prisms, and wavelength selective filters. Alternatively, the source is varied in intensity and/or wavelength as a function of time, such as varying which LED or diode is firing.

Detectors are provided in the form of one or more single element detectors or one or more arrays or bundles of detectors. Exemplary detectors include: indium gallium arsenide (InGaAs), extended InGaAs, lead sulfide (PbS), lead selenide (PbSe), silicon (Si), mercury cadmium telluride (MCT), and the like. Exemplary detectors additionally include arrays of InGaAs, extended InGaAs, PbS, PbSe, Si, MCT, and the like.

Light collection optics, such as fiber optics, lenses, and mirrors, are used in various configurations within a spectrometer to direct light from the source to the detector by way of a sample. The mode of operation is any of diffuse transmission, diffuse reflectance, or transflectance. Due to changes in performance of the overall spectrometer, spectra of reference wavelength standards are optionally collected.

Typically, a wavelength standard is collected immediately before or after the interrogation of the tissue or at the beginning of the day. Optionally, reference values are collected at times far removed from sampling, such as when the analyzer was originally manufactured. Typical reference wavelength standards include: polystyrene, a rare earth oxide, such as holmium, erbium, dysprosium oxide, and any material that has at least one stable and/or sharp spectral feature.

A detailed description of alternative embodiments of analyzers is provided in U.S. patent application Ser. No. 10/472,856 filed Mar. 7, 2003, which is incorporated herein it its entirety by this reference thereto. An algorithm is used in conjunction with an analyzer, as described herein.

An advantage of a spectroscopic based noninvasive analyzer is the ability to collect spectral data, such as replacement, verification, or supplemental spectra, without drawing a new sample. Certain analyzers have an advantage in data collection speed when a large number of data points across a spectral region are used, such as a detector array, Hadamard, or a Fourier transform based spectrometer. Any spectrometer with a multiplexing ability is usable as an analyzer capable of rapid data collection for techniques taught herein. Less preferentially, analyzers that take single wavelength readings as a function of time, such as an analyzer based upon a movable grating, are usable in the invention as taught herein.

EXAMPLE II

An exemplary embodiment of a noninvasive analyzer is provided. An analyzer is configured with a sample module for delivering light to a tissue sample and includes: a tungsten halogen source coupled to a backreflector, an optional first optic for removal of heat and/or unwanted wavelengths of light, a sample interface having a second optic, and at least one fiber optic for collecting light diffusely reflecting from the body. Light is directed from the sample module to the base module, which is preferably integrated with the sample module into a single handheld unit. The base module includes light directing optics, a grating for wavelength separation, and a detector array for detecting and collecting a spectrum of light over at least a portion of the range of about 1100 to 2500 nm. An algorithm coupled with the analyzer is used to, at least, convert the acquired spectra into an analyte property estimation or determination. In one illustrative case, glucose concentration is estimated using near-infrared noninvasive spectra or forearm skin and/or tissue where the spectra includes at least a portion of wavelengths from about 1100 to 1900 nm.

Algorithm

Chemometric calibration and prediction techniques extract an analyte or analyte related signal from acquired spectra through various methods of signal processing and calibration including one or more mathematical models. Multivariate models are developed through the process of calibration on the basis of an exemplary set of spectral measurements known as the calibration set and an associated set of reference property values. Multivariate approaches, requiring an exemplary reference property, such as glucose concentration, for each sample spectrum in a calibration, include partial least squares (PLS) and principal component regression (PCR).

In the preferred embodiment, one or more conditions are used to direct the collection and analysis of replacement, verification, and/or supplemental noninvasive spectra. Examples of these conditions are provided herein in conjunction with benefits of additional data collection and analysis.

Analyzer Performance

In one embodiment of the invention, analyzer performance is improved as a function of analyte property, such as concentration. Spectroscopic methods are rooted in Beer's Law. While Beer's Law fails for spectra of high absorbance matrices and for high scattering matrices, fundamental principles still apply. For example, as the analyte concentration decreases, a direct reading of the signal intensity decreases. As a result, as an analyte concentration decreases, error of the analyzer increases. Processing of spectral data yields an analyte property estimation. Under a set of one or more conditions, replicate measurements are performed to enhance precision and/or accuracy of the estimated analyte property below a threshold level. For example, following a protocol a noninvasive glucose concentration analyzer yields a glucose concentration estimate. If the estimated glucose concentration estimate is below a threshold, then at least one additional spectrum is obtained.

In one instance, a supplemental glucose concentration is obtained from the additional spectrum and the supplemental glucose concentration is mathematically used with the original glucose concentration estimation to yield a new reported glucose concentration having improved estimation characteristics, such as precision, accuracy, or reliability. In another instance, the additional spectrum is combined with the original spectra to form a new spectrum or set of spectra having superior spectral characteristics from which a new glucose concentration is estimated having improved analyte property estimation.

In the case of noninvasive glucose concentration estimation, example threshold levels include: about 70, 90, 110, 130, or 150 mg/dL. Optionally, a second set of conditions is set, such that an additional threshold level is set and one or more still additional spectra are collected based upon the second threshold. For example, if the first threshold is set at 130 mg/dL for having an additional $n_1$ extra spectra being collected, a second threshold is set at a lower concentration, such as about 60, 80, 90, or 110 mg/dL. The second threshold directs $n_2$ additional spectra to be collected, where $n_1$ and $n_2$ are positive integers. Preferably $n_2$ is greater than $n_1$.

In general 1, 2, 3, or more condition levels are set each having its own direction for additional data collection and analysis. Optionally, after any level of additional data collection, the collected data and/or the newly estimated value is used to direct subsequent data collection or analytical approach. In this fashion, the analyzer is operated to enhance performance under conditions, such as where a low signal to noise ratio is obtained or where a analyte property value, such as glucose concentration, is low versus a threshold level. Effectively, this method allows the precision of the analyzer to be enhanced as a function of analyte property. For example, for noninvasive glucose concentration estimation where low glucose concentrations lead to higher errors, the errors are effectively reduced at these lower glucose concentrations. The enhanced precision is preferably reported in Food and Drug Administration or other government controlling body device labeling.

Risk/Precision/Accuracy

In another embodiment of the invention, a first condition is based upon an originally reported noninvasive analyte property estimation compared to a value or property in a look-up table. Estimated glucose concentrations are used to illustrate this condition and the benefit of applying the condition.

At hypoglycemic glucose concentrations, a subject is at acute risk of unconsciousness and even death. A number of current glucose concentration testing meters have reduced precision and accuracy when glucose concentrations are low. This is particularly true for spectroscopic based noninvasive glucose concentration analyzers, which at low analyte concentration have decreasing signal intensity, and hence a lower signal-to-noise ratio. The decreased signal-to-noise ratio and correlated decreased precision enhances the risk of hypoglycemia not being properly detected.

Therefore, a condition is set that below a threshold value or concentration, a supplemental noninvasive glucose concentration is generated. The supplemental glucose concentration is used to enhance the precision of the estimated glucose value through a mathematical calculation, such as averaging, a weighted average, a trimmed mean, or a mathematical transformation.

In a first case, the enhanced precision reduces the probability of reporting an artificially high glucose concentration that leads to non-treatment of the hypoglycemic condition. Similarly, in a second case the enhanced precision reduces the probability of false negative reporting of a hypoglycemic condition. In addition, the condition only applies for a limited range of reported glucose concentrations, thus minimizing the number of times that additional spectra are collected. This reduces overall operating time of the analyzer, cost, and user time. Threshold conditions include glucose concentrations of about 80, 90, 100, 110, 120, 130, 140, and 150 mg/dL. The conditions are optionally stored in a look-up table. The condition compares a preset value, a calculated value, or a value of the look-up table with the original reading. Optionally, the threshold or position of the look-up table is set by the user, manufacturer, or medical professional based upon device labeling, risk tolerance, the individual's state of diabetes mellitus, or medical professional judgment. Optionally, the threshold condition is set based upon the precision of the analyzer. For instance, a higher threshold is optionally set with an analyzer having a poorer precision or larger error.

In general, the error of a reported analyte property estimation is reduced using replicate analysis. The error decreases as the square root of the integral number of measurements N according to Equation 2 below, where $Error_{ol}$ is the error associated with the initial analyte property estimation and $Error_{coadd}$ is the error associated with the co-added errors using the supplemental spectra and associated analyte property estimations.

$$Error_{coadd} = \frac{Error}{\sqrt{N}} \quad (2)$$

Equation 2 assumes random error. In the presence of systemic or nonrandom errors, such as an error associated with the noninvasive sampling process, the actual reduction is error is reduced from the theoretical error reduction of Equation 2.

When multiple observations are available, a number of methods are optionally used to yield a robust estimate of the analyte property. For example, where $\bar{x}$ is an estimated analyte property value, and $x_1, x_2, x_3, \ldots, x_n$ are n analyte measurements preferably collected over a short time period and ordered by value. The $k^{th}$ trimmed mean is calculated according to Equation 3.

$$\bar{x} = \frac{1}{n-2k} \sum_{i=k+1}^{n-k} x_i \quad (3)$$

One or more alternative methods are optionally used to estimate an analyte property from a set of two or more data points. Optimal selection of the mathematical technique depends on the noise structure and correlation between measurements collected in a series. For example, a weighted average of the analyte property values is preferably determined in a case where accuracy changes with additional replicates. In a second exemplary case, a difference between one or more data values is used to qualify individual data points. This technique is used independently or in combination with additional techniques described herein.

Verification

In many instances, it is desirable to have verification of a reported analyte property.

Tradition stick meters and minimally invasive meters are not readily disposed to multiple testing of blood glucose concentration. Traditional stick meters have device labeling that encourages users to check for symptoms to verify results, such as hypoglycemia. This is known to be a very imprecise method of verification, especially as diabetes mellitus progresses in an individual. A true verification requires users to perform a second test. With traditional invasive blood glucose meters, verification testing requires a second lancing procedure using a second test strip. This verification method results in additional pain and roughly doubles the cost due to the use of a second test strip. Minimally invasive techniques typically use a sample that takes a period of time to gather, such as multiple minutes up to twenty or thirty minutes. This makes verification impractical. In many cases, verification is not possible in a short time period. For these reasons, many people do not perform a second test to verify glucose levels that are hypoglycemic, but merely initiate treatment by taking in carbohydrates. This is unfortunate because achieving glucose levels that are 70 to 120 mg/dL are of prime importance in maintaining tight control of diabetes mellitus. Normal physiological glucose concentrations are essential to maintaining a hemoglobin A1C level of less than seven percent.

Some forms of spectrophotometric based noninvasive glucose concentration analyzers offer the ability to verify a glucose concentration reading rapidly through the rapid collection of a replacement or supplemental spectrum and the use of a computer based analysis, supra. This offers the advantage of being able to verify a hypoglycemic glucose concentration reading rapidly. An algorithm is used to invoke additional data collection, such as replacement, verification, and/or supplemental readings based upon one or more conditions. One condition is a glucose concentration below a threshold, such as about 70 to 120 mg/dL. In addition, easily performed, rapid, or automated verification of critical test results is extremely advantageous to clinical management. Use of an automatic mechanism to repeat/verify critical glucose test results without associated barriers of pain and cost has the potential to greatly enhance diabetes mellitus control outcomes.

Critical decisions in diabetes management are necessary when glucose concentrations are greater than about 250 mg/dL. Medication adjustments, such as insulin dosing, testing for urine ketones, avoidance of carbohydrate intake, and avoidance of exercise in type I diabetes are part of the regimen indicated for hyperglycemic values. While current glucose meters recommend verification of test results by associating appropriate and corresponding symptoms, the objective method of verification by repeating the test is seldom performed. The outcome is that many treatment decisions are made in error, such as:

Administering too much or too little of an insulin adjustment dose;

The presence of ketones is not detected and corrective action is not taken quickly, particularly in individuals <45 years of age;

A meal balance is unnecessarily altered; and

Exercise is delayed or omitted.

The conditional approach for replacement, supplemental, or verification data being conditionally collected to replace outliers, verify results, or enhance precision is used to mitigate these issues.

In an additional case, because hypoglycemia is acutely dangerous in an abundance of caution confirmatory glucose concentrations are used to verify the prior reading. The confirmatory data that allow confirmation are controlled by at least one level of conditions. The confirmatory reading is optionally a supplemental reading that is combined with prior readings to enhance analyzer precision and/or accuracy of user presented glucose concentration estimations.

Expected Value

In yet another embodiment of the invention, a set of conditions are used to control replacement, verification, and/or supplemental data collection through use and/or comparison to expected values. An expected value of a reading is generated through a statistical analysis of repeated or successive measurements. Parameters used for expected value estimations include: mean, standard deviation, slope, and elapsed time. A method is implemented for determining when the biological parameter is close to a preset level through a statistical estimate of the confidence limits of a future analyte prediction. For example, the prediction is made through a simple slope, such as a change in the biological parameter over the change in time, estimate based on an exponentially moving average, and the confidence limits are based upon the estimate of precision. Alternately, the prediction is made through a time series analysis. If the associated present property value, such as a glucose concentration, is not within a set confidence interval of the estimated analyte property value, then a condition is optionally set to collect additional data for use as replacement, verification, and/or supplemental analyte property estimations. One set of statistical tools use any combination of mean, standard deviation, and slope of earlier analyte property determinations to estimate future property values, such as a glucose concentration.

In another example, expected values are used to detect the potential for hypoglycemia in diabetics in the near future, such as in about the next 5, 10, 15, 20, 25, or 30 minutes. An optional alarm, such as a visual warning, text, blinking light, or an audible signal is used when this condition is determined.

In yet another example, expected values are used to detect potential outliers through a determination of the statistical consistency of a particular measurement with its expected value. This is of particular importance when low signal-to-noise ratios are used in analyte property determination or when sampling plays a key role in analyte property estimation. For instance, noninvasive glucose concentration estimation is sensitive to skin cleanliness, outside forces on the sampling area, environmental effects, and following set procedures accurately and precisely. Use of expected value analysis is used to remove statistical outliers that results from any of these conditions.

Replicates

In still yet another embodiment of the invention, a condition is set that is optionally repeated, such as in a loop until a second condition is met. For example, a first condition is to collect replicates until an expected value or physiological reasonable analyte property is obtained. A second condition, such as a maximum number of replicates, is preferably set to limit the first condition. For instance, a second condition is to repeat the first condition a set of n times where n is a positive integer greater than 2, such as about 2, 5, 10, or 25. This results in a set of data. Additional analyte property estimation is optionally performed using statistical tools on this set or collection of readings.

Real-Time/Semi-Real-Time

In another embodiment of the invention, a condition is set to provide continuous or nearly continuous blood glucose concentration estimations by repeating on a continual or periodic basis the data collection and analysis steps. In one case, expected values or time series analysis is used prior to display of the stream of glucose concentration estimations to minimize outlier estimations. In a second case, mathematical tools, filters, or analysis are used to improve the precision and/or accuracy of the streaming glucose concentration estimations. Example tools for processing the data stream include: moving averages, slopes, outlier removal techniques, expected value comparison, filtering, smoothing, finite impulse response filters, infinite impulse response filters, and derivatives. In a third case, expected value analysis and outlier removal techniques are used prior to the real-time or semi-real time presentation of the noninvasive glucose concentration estimations. Again, this real time analysis is possible due to the ability of some spectroscopic based analyzers ability to acquire and analyze spectra over a very short time period, such as about one to ten seconds or within a fraction of a second, such as about 10, 50, 100, or 500 milliseconds. This allows real-time or almost real-time assessment of the estimated glucose concentration and the ability to collect one or more subsequent or confirmation readings to be collected and analyzed.

Insulin Dosage

In another embodiment of the invention, a condition is set to optimize the probability that a correct number of units of insulin are injected, ingested, or inhaled to treat a hyperglycemic glucose concentration state. Hyperglycemia is often treated using insulin. In some cases, a small error in the estimated glucose concentration results at an interface region of glucose concentrations between integral number of units of insulin to be administered. For example, a diabetic with a sensitivity of 60 mg/dL glucose concentration change per unit of insulin at a 210 mg/dL glucose concentration needs to decide whether to take one or two units of insulin. One unit leaves them slightly hyperglycemic while two units risks hypoglycemia. The same diabetic at 230 mg/dL faces an easier decision. From 230 mg/dL the use of two units places the diabetic at roughly 110 mg/dL. Clearly the use of one unit is predicted to fail to achieve a normal physiological glucose concentration while the use of three units is predicted to lead to the dangerous state of hypoglycemia. Hence, there are ranges of elevated glucose concentration where enhanced precision of a noninvasive glucose concentration analyzer results in an enhanced probability of the intake of the correct number of units of insulin.

The ranges where increased sensitivity is required is a function of sensitivity of the individual to insulin. Diabetics are often aware or informed of their sensitivity to insulin. Typical sensitivities include about 15, 20, 25, 30, 38, 43, 50, 60, and 75 mg/dL sensitivity per unit insulin. Preferably, a look-up table is generated correlating ranges where increased sensitivity of a noninvasive glucose concentration analyzer is beneficial is readily produced that is a function of insulin sensitivity. Values in the lookup table or calculated on the fly are a function of glucose concentration and sensitivity. Optionally, analyzer error is used in the creation of defining sensitive ranges in the lookup table. Ranges in the lookup table range from about 140 to greater than 400 mg/dL. Key ranges range from about 150 to 250 mg/dL. A condition is set from the look-up table that, for the sensitivity of the individual, if met collects additional spectra to enhance the confidence, precision, and/or accuracy of the noninvasive glucose analyzer. Increasing analyzer performance, using methods describe herein, at the key decision areas or thresholds between integral numbers of units of insulin to be taken increases probability of subsequent glucose concentrations being in the normal physiological range.

Generally, interface glucose concentrations are dependent upon the sensitivity of a subject to insulin. A subject that moves 30 mg/dL per unit of insulin has different interface ranges compared to a subject that move 50 or 70 mg/dL per unit of insulin. Interface regions of most critical importance are about 150 to 250 mg/dL. Interface regions include glucose concentrations from about 120 to 400 mg/dL.

Conditions

Example instances of conditions leading to repeat, replacement, confirmatory, verification, and/or supplementary readings include any of:

An analyte property that is below a threshold;
An analyte property that is above a threshold;
An analyte property outside of an expected value range;
An outlier is detected;
A spectral feature extracted from a spectrum that is out of specification;
A signal-to-noise ratio out of specification;
A glucose concentration reading that is below normal physiological concentration;
A glucose concentration estimation that is above normal physiological concentration;
A glucose concentration that is hypoglycemic;
A glucose concentration that is above ranges typically observed by one having diabetes mellitus; and
A glucose concentration about an interface of decision between integral numbers of units of insulin to administer.

Additional Advantages

A secondary advantage of a control enhancing precision of a noninvasive glucose concentration analyzer through replacement, verification, and/or supplemental glucose concentration determination is to enhance weight control of the subject by avoiding unnecessary food intake to avoid the acute dangers of hypoglycemia when the actual glucose concentration is in the normal range as opposed to a falsely reported hypoglycemic glucose concentration.

Permutations and combinations of the conditions and embodiments described herein are also used to control data collection. For example, a threshold condition is used in combination with a replicate condition.

Those skilled in the art will recognize that the present invention may be manifested in a variety of forms other than the specific embodiments described and contemplated herein. Departures in form and detail may be made without departing from the spirit and scope of the present invention. Accordingly, the invention should only be limited by the Claims included below.

The invention claimed is:

1. A method for enhancing performance of a noninvasive spectroscopy based analyzer, comprising the steps of:
   providing at least one condition, wherein said condition comprises a glucose concentration of less than about ninety milligrams per deciliter;
   collecting at least one noninvasive spectrum using said noninvasive spectroscopy based analyzer;
   determining a first estimated analyte property using said at least one noninvasive spectrum;

if said at least one condition is met, collecting at least one additional spectrum; and using said at least one additional spectrum with either of said at least one noninvasive spectrum, or with said first estimated analyte property to enhance precision of said analyzer when said glucose concentration is hypoglycemic.

2. The method of claim 1, wherein said step of using said at least one additional spectrum replaces said at least one noninvasive spectrum.

3. The method of claim 1, wherein said step of using said at least one additional spectrum verifies said estimated analyte property.

4. The method of claim 1, wherein said step of using said at least one additional spectrum supplements said at least one noninvasive spectrum.

5. The method of claim 1, wherein said additional spectrum is collected using a multiplexed spectroscopy based analyzer.

6. The method of claim 1, wherein said at least one condition comprises any of:
an expected value;
an estimated analyte concentration;
an upper threshold;
a lower threshold; and
a threshold range.

7. The method of claim 1, wherein said condition comprises:
a number of replicates.

8. The method of claim 1, wherein said condition comprises:
a specification.

9. The method of claim 8, wherein said specification comprises:
a signal-to-noise ratio.

10. The method of claim 1, wherein said noninvasive spectrum comprises wavelengths in the near-infrared region.

11. The method of claim 10, wherein said near-infrared regions comprises wavelengths at least partially within the region of about 1100 to 1900 nm.

12. The method of claim 1, wherein said condition controls either semi-continuous or continuous analysis of said analyte property.

13. An apparatus for noninvasive analysis of a body part, comprising
a noninvasive analyzer;
an algorithm operating in conjunction with said analyzer; and
at least one condition in said algorithm, wherein said condition comprises a glucose concentration of less than about ninety milligrams per deciliter;
wherein said analyzer operates to collect at least one noninvasive spectrum and wherein said algorithm determines an estimated analyte property of the body part using said noninvasive spectrum; and
wherein if said at least one condition is met, said analyzer collects at least one additional spectrum and said at least one additional spectrum is used with either of said at least one noninvasive spectrum or said estimated analyte property to enhance precision of said analyzer when said glucose concentration is hypoglycemic.

14. The apparatus of claim 13, wherein said analyzer comprises at least:
a near-infrared source emitting light over at least 1100 to 1900 nm; and
a detector array.

15. The apparatus of claim 13, wherein said at least one additional spectrum comprises any of:
at least one replacement spectrum;
at least one verification spectrum; and
at least one supplemental spectrum.

16. The apparatus of claim 13, wherein said enhanced performance comprises:
an improved precision.

17. The apparatus of claim 13, wherein said at least one condition comprises any of:
an expected value; and
a threshold value.

18. The apparatus of claim 17, wherein said enhanced performance comprises any of:
an improved precision above said threshold value;
an improved precision below said threshold value;
an improved precision at a glucose concentration sensitive to integral insulin unit dosage;
an improved precision about a value maintained in a look-up table.

19. The apparatus of claim 13, wherein said algorithm comprises:
an outlier identification routine.

20. The apparatus of claim 19, wherein said outlier identification routine uses said additional spectrum.

21. The apparatus of claim 13, wherein said analyzer comprises at least one of:
a multiplexed optical path; and
a detector array.

22. The apparatus of claim 13, wherein said noninvasive analyzer comprises:
a handheld unit.

23. A method for reducing non invasive analyte property estimation error, comprising the steps of:
providing at least one set of conditions, wherein said condition comprises an expected value generated using successive measurements, wherein said expected value indicates a potential for hypoglycemia in the next about 15 minutes;
collecting a noninvasive spectrum using a noninvasive spectroscopy based analyzer;
estimating an analyte property using said spectrum;
recording said analyte property in a set of estimations;
if said set of conditions is met repeating said steps of collecting, estimating, and recording; and
generating an analyte property estimation using said set of estimations;
wherein said set of estimations comprises at least two estimations of said analyte property.

24. A method for reducing noninvasive analyte property estimation error, comprising the steps of:
providing at least one set of conditions, wherein said set of conditions comprises a number of replicates greater than ten, wherein each of said replicates comprise acquisition within about five hundred milliseconds;
collecting a noninvasive spectrum using a noninvasive spectroscopy based analyzer;
estimating an analyte property using said spectrum;
if said set of conditions is met, recording said analyte property estimation;
repeating said steps of collecting and estimating; and
updating said recorded analyte property estimation using said analyte property estimation and said recorded analyte property estimation.

* * * * *